United States Patent [19]

Somerville et al.

[11] Patent Number: 4,460,358

[45] Date of Patent: Jul. 17, 1984

[54] COMBINED LOAD AND LATCH MECHANISM FOR FLUID FLOW CONTROL APPARATUS

[75] Inventors: Alvis J. Somerville, San Diego; Richard B. Conley, Jamul; Robert B. Truitt, San Diego, all of Calif.

[73] Assignee: IVAC Corporation, San Diego, Calif.

[21] Appl. No.: 204,772

[22] Filed: Nov. 7, 1980

[51] Int. Cl.³ .............................................. A61M 5/00
[52] U.S. Cl. ........................... 604/250; 128/DIG. 13; 251/7; 222/450; 604/245; 604/34
[58] Field of Search ........... 128/214 R, 214 E, 214 F, 128/214.2, DIG. 13; 251/7, 9; 222/450–452, 445; 604/34, 65–67, 153, 245–246, 250

[56] References Cited

U.S. PATENT DOCUMENTS

| | | | |
|---|---|---|---|
| 3,335,753 | 8/1967 | Kiser | 251/9 X |
| 3,756,556 | 9/1973 | Georgi | 251/7 |
| 4,261,356 | 4/1981 | Turner | 128/214 R |

FOREIGN PATENT DOCUMENTS 2733702  2/1979  Fed. Rep. of Germany ... 128/214 E

Primary Examiner—Dalton L. Truluck
Attorney, Agent, or Firm—Fulwider, Patton, Rieber, Lee & Utecht

[57] ABSTRACT

A combination load and latch mechanism for fluid flow control apparatus, wherein a latch mounted for pivotal movement may be manually opened to disengage an electromechanical manipulating device to permit loading or unloading a feeding tube, the latch automatically closing and the device re-engaging upon release of the latch. The latch includes a slotted side wall that defines a retaining surface for capturing the tube relative to the manipulating device, and a cam surface upon which the tube acts during loading to cam the latch open. Means are included for sensing movement of the latch prior to any disengagement of the manipulating device.

19 Claims, 8 Drawing Figures

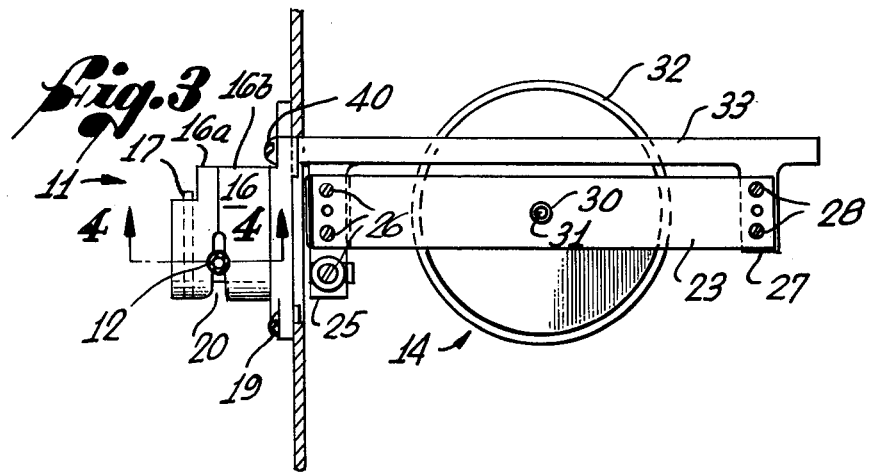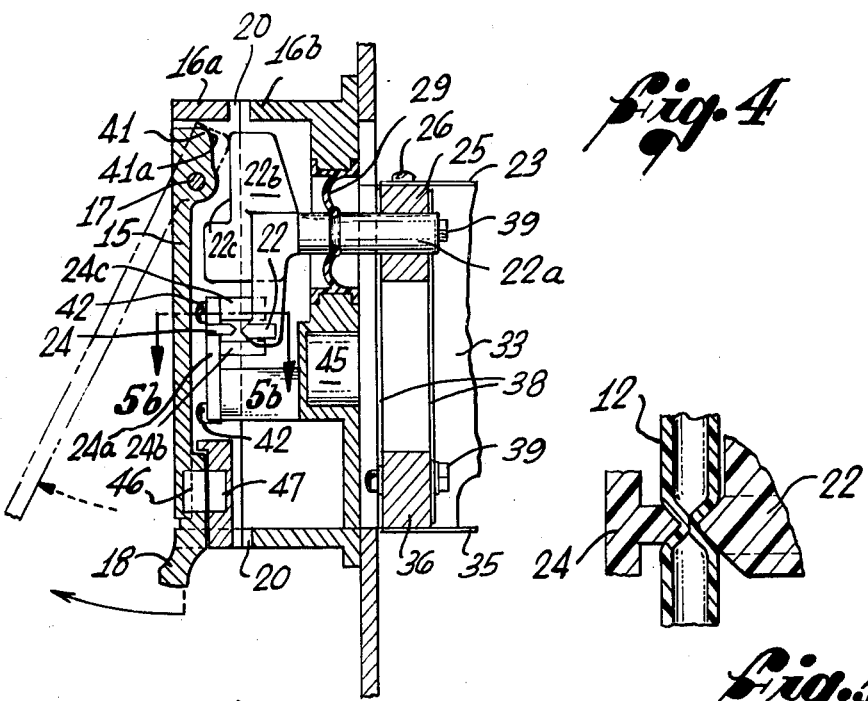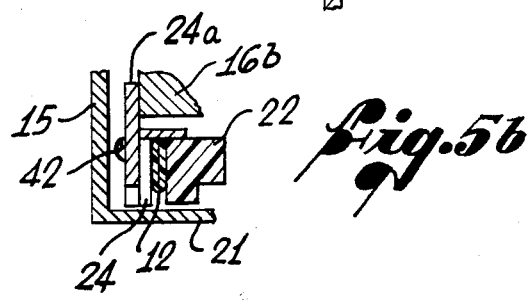

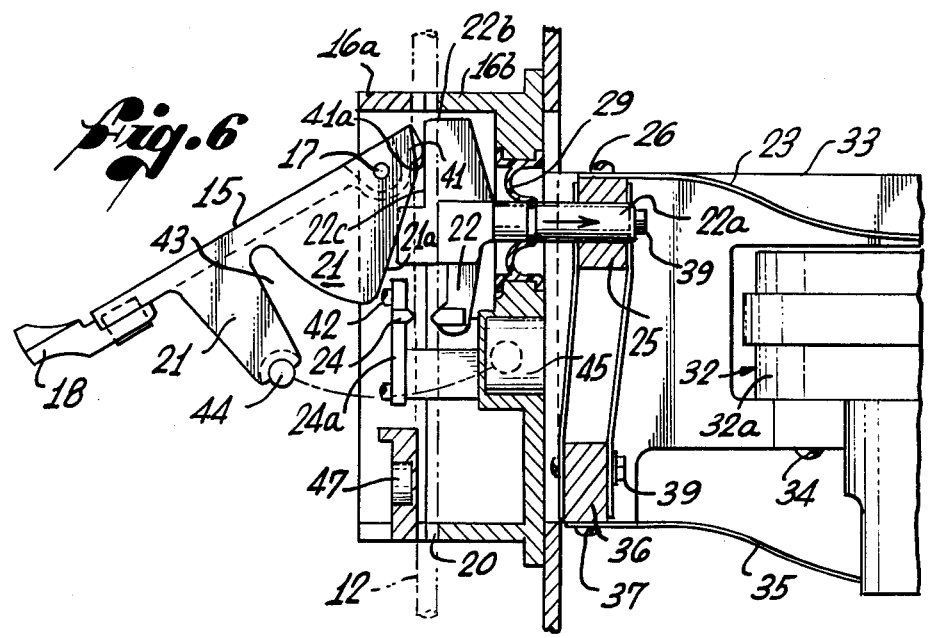
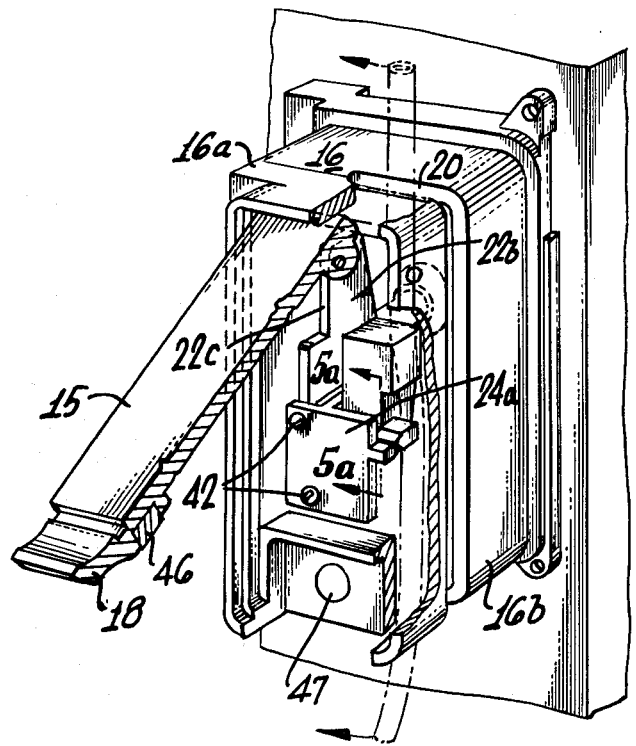

COMBINED LOAD AND LATCH MECHANISM FOR FLUID FLOW CONTROL APPARATUS

BACKGROUND OF THE INVENTION

This invention relates generally to improvements in fluid flow control systems and, more particularly, to a new and improved combination load and latch mechanism for installing and securely capturing a fluid feeding tube in operative relation to an appropriate electromechanical output device. The invention has particular application in connection with instrument systems for administering parenteral fluids to the human body.

The administration of parenteral fluids (referred to herein as "intravenous administration" or "IV administration") to human patients conventionally involves use of a solution administration set. The set typically is a disposable plastic product, and comprises a drop chamber adapted to be connected to a fluid source, a length of tubing extending from the chamber to the patient and a valve mechanism, such as a roller clamp on the tubing.

In recent years, a variety of mechanical and electrical monitoring systems, controllers and infusion pumps have been developed to accomplish the tasks of sensing and regulating the rate of fluid flow into the human body. Such apparatus generally include an electromechanical output device for manipulating the IV tube in a prescribed manner, as by using tube pinchers to repetitively open and close the tube for controlling the flow of fluid through the tube. Some of the apparatus have also been capable of activating alarms when an out-of-limit condition exists, thus freeing medical personnel to some extent for other duties.

However, while such apparatus have generally served their purpose, there is a continuing need for improvement from the standpoint of convenience in loading the IV tube into the apparatus and ensuring that the tube remains engaged with, and therefore under the control of, the electromechanical output device. In particular, for example, many of these apparatus are housed in a case having a hinged door forming a front panel, which must be opened for loading the IV tube in a position to be manipulated by the output device. A portion of the back side of the door often serves as a hard clamping surface or fixed anvil against which the output device presses the tube for manipulation when the door is closed. Thus, the door forms an operational part of the electromechanical output device.

With the aforedescribed structural arrangement, precautions are necessarily taken to ensure that the roller clamp or other valve mechanism is shut off before the door is opened or, while the tube is in place, that the door is securely closed. Fluid flow to the patient might otherwise be at an uncontrolled rate.

Hence, those concerned with the development and use of fluid administration systems, and particularly those concerned with the design of IV administration systems, recognize the need for further improvement in the loading and latching subsystems of IV administration systems.

SUMMARY OF THE INVENTION

Briefly, and in general terms, the present invention resides in a new and improved combination load and latch mechanism for convenient loading and secure latching of an IV tube in position for manipulation by an electromechanical output device, wherein the output device is disengageable from the IV tube in response to a manual actuating force, but is biased to automatically re-engage the tube when the manual force is removed. The mechanism provides a more secure arrangement for aiding in ensuring against uncontrolled flow resulting from loss of engagement between the IV tube and the output device.

More particularly, the load and latch mechanism of the present invention includes a latch mounted for movement between a fully closed position, in which the output device is engaged and freely operable to manipulate the IV tube, and a fully open position, in which the latch disengages the output device to permit loading and unloading of the IV tube. The latch is movable to the fully open position by manual actuation, for loading or unloading the IV tube, and both the latch and the output device are biased, respectively, for automatic return to the closed position and for re-engagement upon removal of the manual actuating force. In this regard, the latch also facilitates momentary manual override or disengagement of the output device by the operator, after the IV tube is loaded, for the purpose of priming the IV set or confirming the existence of an open fluid path through the IV tube during infusion. The mechanism, moreover, provides for semi-automatic loading of the IV tube in which the action of inserting the tube into position tends to drive the latch momentarily open, the latch being resistant to opening after the IV tube is loaded, except in response to deliberate manual operation of the latch. In a further aspect of the invention, movement of the latch is sensed in advance of the output device actually becoming disengaged so that medical personnel can be warned in advance of a possible problem.

In the presently preferred embodiment, by way of example, the latch is mounted for pivotal movement within the face of a frame, which has a tube receiving channel formed in one side wall and opening out the opposite end walls of the frame. Disposed within the frame, in the channel, is a tube pincher normally biased by an electromechanical actuator to squeeze the IV tube closed against an anvil, the actuator being operable to repetitively open the IV tube for controlled fluid flow through the tube. The latch has a camming surface at one end that engages the tube pincher to drive back the pincher from the anvil as the latch is manually pivoted from its fully closed position to the fully open position. With the latch in the fully open position, the IV tube can be loaded in or out, or as mentioned above, the tube pincher is conveniently disengaged for priming the IV set or for determining whether the fluid path through the tube is open. Upon release, the latch automatically returns to the fully closed position and the tube pincher returns to its clamped-off state, urged by the normal biasing of the electromechanical actuator.

A side wall depending from the latch, normal to the face of the frame, acts as a movable closure or retaining surface to positively capture the IV tube in the channel. The side wall, which is received into the frame and underlies the channel opening when the latch is closed, is provided with a clearance slot into which the tube pincher and the anvil extend to safeguard against migration of the tube out of engagement with the pincher and anvil.

Semi-automatic loading of the IV tube, as referred to above, is achieved by appropriate shaping of the upper edge surface of the side wall, whereby the action of inserting the IV tube into the channel tends to cam the side wall out of the channel opening and thereby drive the latch to an open position. Upon complete insertion into the channel between the tube pincher and the anvil, the tube disengages the side wall, whereupon the latch of course automatically closes.

The side wall of the latch carries a magnetic pellet by means of which a suitable sensor, such as a Hall effect device, cam sense whether the latch is fully closed or not. Importantly, the latch has to be moved to a partially open position before the shoulder on the latch engages the tube pincher to drive it back from the anvil. The sensor provides early detection of latch movement, between the fully closed and partially open positions, so that medical personnel can be warned before disengagement between the tube pincher and the IV tube occurs.

The above and other objects and advantages of this invention will become apparent from the following more detailed dscription, when taken in conjunction with the accompanying drawings of an illustrative embodiment.

BRIEF DESCRIPTION OF THE DRAWINGS

FIG. 3 is a top plan view similar to FIG. 2;

FIG. 4 is a fragmentary sectional view taken along line 4—4 in FIG. 3, and illustrates the latch in the fully closed position, a partially open position being shown in phantom;

FIG. 5a is an enlarged fragmentary sectional view taken along line 5a—5a in FIG. 7, while FIG. 5b is an enlarged fragmentary sectional view taken along line 5b—5b in FIG. 4, both figures showing the IV tube in position between the tube pincher and the anvil for purpose of clarity;

FIG. 6 is a fragmentary sectional view similar to FIG. 4, and illustrates the state of the mechanism with the latch in the fully open position, the latch side wall being shown for purpose of clarity; and FIG. 7 is a perspective view of the tube pincher and the anvil of the electromechanical output device, with the latch, shown in an open position, and the mechanism frame partially broken away.

DESCRIPTION OF THE PREFERRED EMBODIMENT

Figure 1:
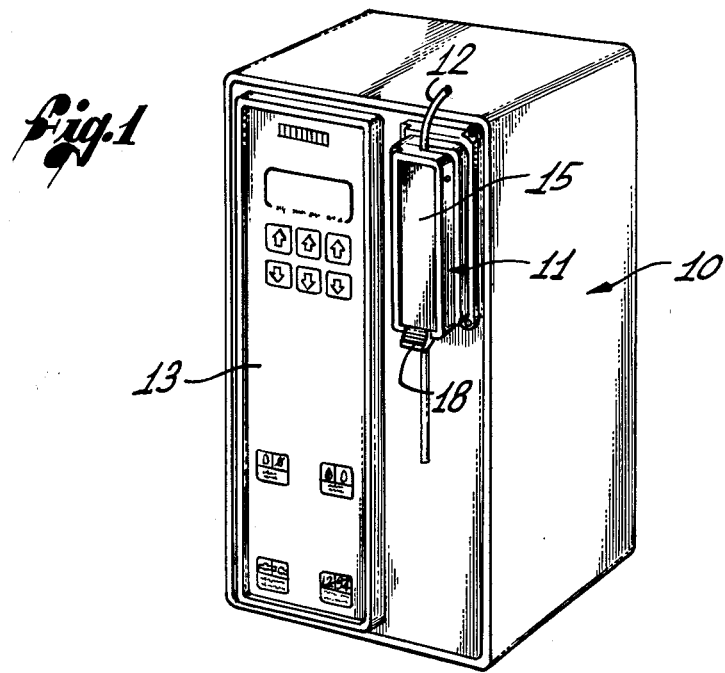
FIG. 1 is a perspective view of a representative IV controller utilizing a combination load and latch mechanism embodying the principles of the present invention.

Referring now to the drawings for the purpose of illustrating the presently preferred embodiment of the invention, and particularly to FIG. 1 thereof, there is shown a fluid flow controller 10 including a combination load and latch mechanism 11 providing for simplified loading and secure latching of an IV tube 12 into position for manipulation by an electromechanical output device, such as the device described below. In the ensuing description, references will be made to the term "IV", normally connoting intravenous adminstration, although it is to be understood that this is by way of example only, the present invention having application to other forms of administration.

The IV tube 12, only a small portion of which is shown in the drawing, is part of an IV set, as earlier described, extending upstream from the controller 10 to a drip chamber and an inverted bottle of liquid and leading downstream from the controller to the patient. A control panel 13 on the face of the controller 10 includes various operating switches, controls and indicators, which need not be described individually herein to impart an understanding of the present invention.

A subassembly consisting of the load and latch mechanism 11 interconnected with the electromechanical output device, indicated generally by reference numeral 14, is illustrated in FIGS. 2 through 7 of the drawings. The mechanism 11 includes an elongate latch 15 mounted in a frame 16 on a pin 17 for pivotal movement, the latch on its lower end having an extended finger grip forming a handle 18 by which the latch can be pulled outwardly and upwardly to an open position. For ease of manufacture, the frame is divided into an outer frame 16a, in which the latch member 15 is mounted, and an inner frame 16b joined to the outer frame by screws (not shown). The inner frame 16b in turn is mounted to the controller housing by screws 19.

Both the outer frame 16a and the inner frame 16b are cut away along one contiguous side so that their joinder forms a longitudinal channel 20, extending through the opposite ends of the frame, in which the IV tube is received for manipulation by the output device 14. A side wall 21 depends normal to the face of the frame 16 along one side of the latch 15 and is receivable into the frame 16 to form a closure for the channel 20, underlying the channel opening when the latch is in the fully closed position. Although the side wall 21 illustrates an important aspect of the invention and will be described in detail below, it will simply be noted at this point that lifting the latch 15 by its handle 18 to a fully open position (FIG. 6) moves the side wall outwardly to clear the channel 20 for loading and unloading the IV tube 12 therein.

The output device 14 includes a tube pincher 22 disposed in the frame 16, within the channel 20, for back and forth vibrating movement in a substantially linear path, to cyclically clamp off and open the IV tube 12, thereby permitting fluid flow at a controlled rate through the tube. The pincher 22 is normally spring-biased by the relaxed condition of a flat ribbon spring 23 to clamp off the IV tube 12 against an anvil 24. The ribbon spring 23 has a free end affixed to a floating corner block 25, to which a connecting shaft 22a integrally formed with the tube pincher 22 is also secured, as by screws 26, and the opposite end of the ribbon spring is secured to a fixed anchor block 27, as by screws 28. A flexible grommet 29 is received about the connecting shaft 22a in a throughbore in the inner frame 16b, through which the shaft extends, to seal the inside of the controller against accidental fluid spills.

The center of the spring 23 is rigidly connected by a coupling 30 to a shaft 31 of an electromechanical actuator 32, such as a voice coil actuator or solenoid, having its stator magnet 32a secured in an opening in a mounting plate 33 by screws 34. The end of the actuator shaft 31 remote from the ribbon spring 23 is secured by a similar coupling (not shown) to one end of a shorter ribbon spring 35, which extends to a second fixed anchor block 36 where it is secured by screws 37. A pair of parallel ribbon springs 38 extend between the floating corner block 25 and the second fixed anchor block 36, the springs being connected to opposite sides of both blocks by a plurality of screws 39. The fixed anchor blocks 27, 36 are rigid projections integrally formed on the mounting plate 33, which itself is secured at one end by screws 40 to the inner frame 16b.

In operation of the output device 14, all of the ribbon springs 23, 35, 38 begin in a relaxed state with the tube pincher 22 clamping off the IV tube 12. When the electromechanical actuator 32 is electrically energized, the shaft 31 simultaneously flexes both of the individual ribbon springs 23, 35 to which it is attached, as shown in phantom in FIG. 2, causing the free floating corner block 25, and hence the shaft 22a and the tube pincher 22, to move inwardly, opening the IV tube 12 to fluid flow. The tube pincher 22 is operated cyclically in this fashion to control the rate of flow through the IV tube 12.

A more detailed description of the output device 14 and a description of a suitable system for providing appropriate electrical signals to the actuator 32 are set forth, respectively, in U.S. Pat. No. 3,756,556 entitled Fluid Flow Control Apparatus, issued Sept. 4, 1973, inventor Heinz W. Georgi, and in U.S. Pat. No. 4,037,598 entitled Method and Apparatus For Fluid Flow Control, issued July 26, 1977, inventor Heinz W. Georgi, both of which descriptions are incorporated herein by reference as though set forth in full.

In accordance with the invention, the latch 15 is moveable from a fully closed position, shown in full lines in FIG. 4, to the aforementioned fully open position, as shown in FIG. 6, to manually disengage or drive back the tube pincher 22 from the anvil 24, against the biasing force of the ribbon springs 23, 35, 38. To this end, the latch 15 is provided with a shoulder 41 at its upper end, above the pin 17, on which a cam surface 41a is formed. The tube pincher 22 includes an integral upright portion 22b having a forwardly facing edge 22c aligned for camming engagement by the cam surface 41a of the shoulder 41 as the latch 15 is pulled outwardly and upwardly. It will be noted that operation of the latch 15 does not effect movement of the anvil 24 as the anvil, which is integrally formed on a plate 24a, is fixedly mounted to the inner frame 16b by screws 42.

As previously mentioned, the latch 15 includes a side wall 21 receivable, when the latch is fully closed, into the frame 16, where it underlies the opening along the side of the frame formed by the channel 20. This side wall 21 serves as part of a tube retaining surface, positively capturing the feeding tube 12 in the channel 20 from one side and preventing it from possibly migrating out from between the tube pincher 22 and the anvil 24. This is important since such migration would result in a loss of control leading to uncontrolled flow in the feeding tube 12.

Figure 2:
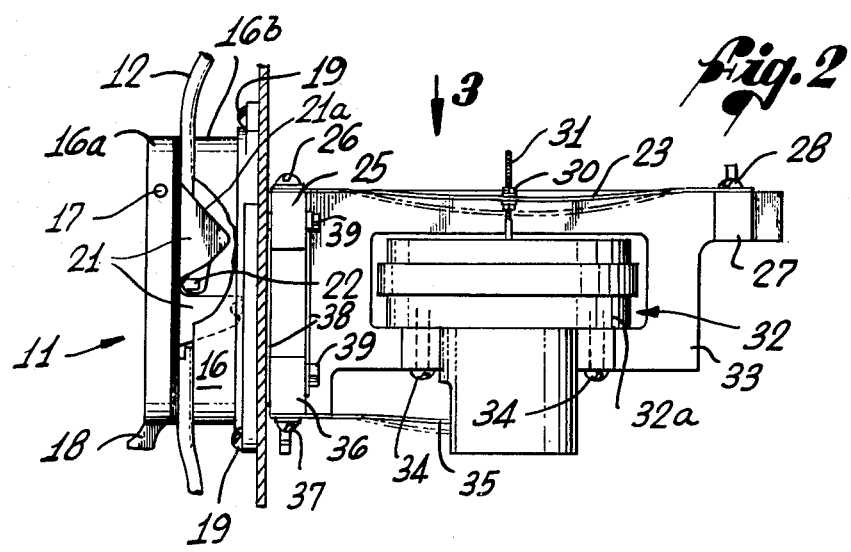
FIG. 2 is a side elevational view of a subassembly removed from the controller of FIG. 1, showing the mechanism with a side wall of the frame partially broken away to illustrate the side wall on the latch, the electromechanical output device shown interconnected with the mechanism.

For added protection against feeding tube migration, both the tube pincher 22 and the anvil 24 extend laterally into the plane defined by the side wall 21, which has a generally arcuate clearance slot 43 for receiving the extended ends of the pincher and the anvil (FIGS. 2 and 6). The opposite ends of the tube pincher 22 and the anvil 24 are similarly extended, and a pair of fingers 24b, shown in FIG. 4, depend from the anvil plate 24a to straddle these extended pincher and anvil ends and thereby form a retaining surface on the other side of the channel 20. Sufficient clearance is provided between the fingers 24b and the tube pincher 22 so that the fingers do not interfere with movement of the pincher. The upright portion 22b of the tube pincher 22 is vertically aligned with the fingers 24b so that the upright portion also functions as an extension of the retaining surface on the inside of the channel 20.

The portion of the side wall 21 below the clearance slot 43 resembles an arm and carries a magnetic pellet 44 at its free end. When the latch 15 is in the fully closed position, the pellet 44 is aligned laterally with a compartment 45 formed in the back wall of the inner frame 16b. The compartment 45 opens to the rear and houses a Hall effect device (not shown), which is responsive to the position of the pellet 44 to sense whether the latch 15 is fully closed. Since the inner frame 16b is cast of aluminum, as is the outer frame 16a and the latch 15, the Hall effect device is effective to sense the pellet 44 through the relatively thin wall defining the compartment 45.

The lower inside end portion of the latch 15 carries a recessed steel slug 46 which cooperates, when the latch 15 is fully closed, with another magnetic pellet 47 recessed into the outer frame 16a to provide a magnetic catch for the latch.

To facilitate loading of the IV tube 12 into the channel 20, the top edge of side wall 21 is shaped to form a camming surface 21a by means of which the action of inserting the tube into the channel tends to cam the latch 15 open. Specifically, this loading operation is performed by inserting the feeding tube 12 into the upper portion of the channel 20, above the camming surface 21a, and then stretching the tube taut while drawing it into the channel with a wiping action. In order to begin movement of the latch 15, it may be necessary to manually release it from the aforementioned magnetic catch. The tautly stretched portion of the feeding tube 12 engages the camming surface 21a and tends to drive it out of the channel 20, causing the latch 15 to pivot open.

Continued insertion of the feeding tube 12 into the channel 20 results in the cam surface 41a of the latch shoulder 41 driving back the tube pincher 22 from the anvil 24. The feeding tube 12 disengages the camming surface 21a of the side wall 21 as soon as the side wall has been driven clear of the channel opening. With the feeding tube 12 then fully inserted into the channel 20 and received between the tube pincher 22 and the anvil 24, the combined forces of gravity and the flexed ribbon springs 23, 35, 38 bias the latch 15 for return to the fully closed position with the side wall 21 closing off the channel opening to capture the tube. Simultaneously, the ribbon springs 23, 35, 38 also drive the tube pincher 22 forward to its normal position clamping off the feeding tube 12 against the anvil 24. The generally flat, horizontal orientation of the lower edge of the side wall 21 renders it resistant to being inadvertently cammed up for unloading of the IV tube. Any accidental pulling of the IV tube is likely to be caused by patients, who generally are lying down at a level below the controller.

In addition to the aforedescribed automatic loading technique, several other advantages of the present invention are readily discerned. For example, standard medical procedures require that the IV set be primed, i.e., filled with fluid and purged of air, before being connected to the patient. Once the feeding tube is loaded, the standard roll-clamp is opened and the latch 15 can be manually moved to the fully open position to intentionally create a free flow condition for priming the IV set. So long as the latch is being lifted to its full extent, the free flow condition will endure, and upon its release, the latch automatically returns to the fully closed position and the tube pincher is driven forward to clamp-off the IV tube.

Likewise, after the IV set has been primed and infusion to the patient is in process, the mechanism provides a ready means for determining whether the fluid path is open. Apparatus, such as the IV controller shown herein for illustration, are generally capable of detecting a variety of alarm conditions and shutting down the output device to cease liquid flow to the patient as a precaution. In some cases, an occlusion in the fluid path will itself have precipitated the alarm. Medical personnel attempting to determine the source of the alarm condition can, by simply lifting the latch to its fully open position and placing the IV tube in free flow, quickly determine whether an occlusion is the problem. Again, release of the latch automatically returns the tube pincher to the clamped-off position.

As best shown in FIGS. 4 and 6, another advantage of the present invention is that movement of the latch 15 is sensed before any disengagement of the tube pincher 22 occurs. This is because the latch shoulder 41 is spaced from the pincher upright 22b when the latch is fully closed, so that some movement of the latch is required before the shoulder engages the upright. Any significant movement of the latch is, of course, immediately sensed by the Hall effect sensor and appropriate visual and aural alarms can be triggered as a warning to medical personnel that a potentially dangerous condition exists before control of the IV tube is lost.

The new and improved combination load and latch mechanism of the present invention is extremely convenient, reliable and secure. The mechanism provides semi-automatic loading of an IV tube and enhanced safety by ensuring against loss of control, while permitting intentional momentary disengagement of the electromechanical output device to enable priming and verification of an open fluid path.

It will be apparent from the foregoing that, while a particular form of the invention has been illustrated and described, various modifications can be made without departing from the spirit and scope of the invention. Accordingly, it is not intended that the invention be limited except as by the appended claims.

We claim:

1. In a fluid flow control apparatus for controlling the parenteral administration of liquids through a feeding tube from a liquid source to a patient, the combination comprising:
    electromechanical output means for manipulating the feeding tube to vary the flow of liquid in the feeding tube, said output means including biasing means for applying a bias force normally urging said output means to a position for engagement with the feeding tube; and
    a latch mounted for movement between an open position and a closed position, said latch in said open position urging said output means to a position for disengagement with the feeding tube, and said biasing means urging said output means to automatically return to said position for engagement with the feeding tube upon movement of said latch to said closed position, said latch further including a wall defining one side of a channel for capturing the feeding tube in position for manipulation by said output means when said latch is in said closed position.

2. Apparatus as set forth in claim 1, wherein said wall further includes a clearance slot into which at least a portion of said output means is received when said latch is in said closed position.

3. Apparatus as set forth in claim 1, wherein said wall further includes a camming surface adapted for engagement with the feeding tube as the tube is being inserted into said channel, such that said latch is biased to said open position by insertion of the tube.

4. Apparatus as set forth in claim 3, wherein said biasing means exerts a bias force biasing said latch for return to said closed position as the feeding tube disengages said camming surface upon entering said channel.

5. Apparatus as set forth in claim 1, wherein movement of said latch to said open position moves said wall permitting the feeding tube to be inserted into and removed from said channel.

6. Apparatus as set forth in claim 1, wherein said latch is mounted for pivotal movement between said open position and said fully closed position.

7. Apparatus as set forth in claim 6, and further including:
    sensing means for sensing movement of said latch from said closed position prior to disengagement of said output means.

8. In a fluid flow control apparatus for controlling the parenteral administration of liquids through a feeding tube from a liquid source to a patient, the combination comprising:
    tube clamping means for squeezing the feeding tube;
    clamping actuator means, coupled to said tube clamping means, for applying a bias force causing said tube clamping means to normally squeeze the feeding tube closed and thereby prevent liquid flow through the feeding tube, said clamping actuator means causing said tube clamping means to repetitively open the feeding tube to allow controlled liquid flow through the feeding tube; and
    clamping disengagement means mounted adjacent said tube clamping means for movement between a fully open position and a fully closed position, said clamping disengagement means in said fully closed position permitting said tube clamping means to open and close the feeding tube in response to said clamping actuator means, and said clamping disengagement means in said fully open position urging said tube clamping means against said bias force to disengage said tube clamping means and thereby permit loading and unloading of the feeding tube relative to said tube clamping means,
    said clamping disengagement means moveable from said fully closed position to said fully open position responsive to a manual actuating force, said clamping disengagement means remaining in said fully open position only by continued application of said manual actuating force, and said clamping disengagement means urged by said bias force to automatically return to said fully closed position upon removal of said manual actuating force.

9. Apparatus as set forth in claim 8, wherein said disengagement means comprises a latch.

10. Apparatus as set forth in claim 9, wherein said latch further includes a camming surface for bising said tube clamping means to a position of disengagement when said latch is in the fully open position.

11. Apparatus as set forth in claim 10, wherein said clamping actuator means exerts a bias force biasing said latch for return to the fully closed position upon removal of said manual actuating force.

12. Apparatus as set forth in claim 9, wherein said latch includes a wall defining one side of a channel capturing the feeding tube in position for manipulation by said tube clamping means.

13. Apparatus as set forth in claim 12, wherein movement of said latch to the fully open position moves said wall permitting the feeding tube to be inserted into and removed from said channel.

14. Apparatus as set forth in claim 13, wherein said wall further includes a camming surface adapted for engagement with the feeding tube as the tube is being inserted into said channel, such that said latch is biased to the fully open position by insertion of the tube.

15. Apparatus as set forth in claim 14, wherein said clamping actuator means exerts a bias force biasing said latch for return to the fully closed position as the feeding tube disengages said camming surface upon entering said channel.

16. Apparatus as set forth in claim 12, wherein said latch is mounted for pivotal movement between said fully open position and said fully closed position.

17. Apparatus as set forth in claim 16, wherein said wall further includes an arcuate clearance slot into which at least a portion of said tube clamping means is received when said latch is in the fully closed position.

18. Apparatus as set forth in claim 9, wherein said latch is movable to a partially open position without disengagement of said tube clamping means.

19. Apparatus as set forth in claim 18, and further including:
    sensing means for sensing movement of said latch from said fully closed position to said partially open position.

* * * * *